US012672207B2

(12) United States Patent
Shoched

(10) Patent No.: US 12,672,207 B2
(45) Date of Patent: *Jun. 30, 2026

(54) METHOD AND APPARATUS FOR VAPORIZING LIQUIDS OR THE LIKE WITH A CONCEALABLE VAPORIZER PEN

(71) Applicant: DES Products Ltd, Lambertville, MI (US)

(72) Inventor: Dana E. Shoched, Lambertville, MI (US)

(73) Assignee: DES PRODUCTS LTD, Lambertville, MI (US)

( * ) Notice: Subject to any disclaimer, the term of this patent is extended or adjusted under 35 U.S.C. 154(b) by 177 days.

This patent is subject to a terminal disclaimer.

(21) Appl. No.: 16/598,082

(22) Filed: Oct. 10, 2019

(65) Prior Publication Data

US 2020/0260528 A1 Aug. 13, 2020

Related U.S. Application Data

(63) Continuation of application No. 15/614,127, filed on Jun. 5, 2017, now Pat. No. 10,448,456.

(51) Int. Cl.
*A24F 40/95* (2020.01)
*A24F 40/10* (2020.01)
(Continued)

(52) U.S. Cl.
CPC ........... *H05B 1/0244* (2013.01); *A24F 40/50* (2020.01); *A24F 40/60* (2020.01); *A24F 40/95* (2020.01); *A61M 11/042* (2014.02); *A61M*

*15/0023* (2014.02); *A61M 15/06* (2013.01); *G01D 7/00* (2013.01); *A24F 40/10* (2020.01);
(Continued)

(58) Field of Classification Search
None
See application file for complete search history.

(56) References Cited

U.S. PATENT DOCUMENTS 8,739,786 B2    6/2014   Postma
9,197,726 B2    11/2015  Stanimirovic et al.
(Continued)

FOREIGN PATENT DOCUMENTS

WO          03/082063 A1    10/2003

*Primary Examiner* — Katherine A Will
(74) *Attorney, Agent, or Firm* — Volpe Koenig

(57)          ABSTRACT

A compact electronic vaporizer is provided herein with a concealable articulating vaporizer pen for vaporization of liquids that articulates between a closed position inside a protective case and an open position outside of the protective case. The protective case contains a deployable power adaptor configured to charge a battery. The battery may be activated by a battery switch within the protective case. A push button on the exterior of the protective case simultaneously articulates the concealable articulating vaporizer pen and activates the battery switch on the battery to turn on the vaporizer. The vaporizer includes a variable voltage controller configured to select a variable voltage of the battery, providing an improved vaporization experience as the user can select an optimum voltage at which to vaporize. The vaporizer is configured for right-handed users and contains a mouthpiece with round-tip opening to provide for more convenient and ergonomic vaporization by the user.

20 Claims, 13 Drawing Sheets

(51) Int. Cl.

| | |
|---|---|
| *A24F 40/50* | (2020.01) |
| *A24F 40/60* | (2020.01) |
| *A61M 11/04* | (2006.01) |
| *A61M 15/00* | (2006.01) |
| *A61M 15/06* | (2006.01) |
| *G01D 7/00* | (2006.01) |
| *H05B 1/02* | (2006.01) |
| *H02J 7/00* | (2006.01) |
| *H02J 7/82* | (2026.01) |
| *H02J 7/90* | (2026.01) |

(52) U.S. Cl.

CPC .............. *A61M 2205/3653* (2013.01); *A61M 2205/8206* (2013.01); *A61M 2209/045* (2013.01); *H02J 7/825* (2026.01); *H02J 7/855* (2026.01); *H02J 7/971* (2026.01)

(56) References Cited

U.S. PATENT DOCUMENTS

| | | | |
|---|---|---|---|
| 9,806,754 B1 | 10/2017 | Hodge | |
| 2014/0096781 A1* | 4/2014 | Sears ...................... | A24F 40/50 131/328 |
| 2014/0123990 A1* | 5/2014 | Timmermans .......... | A24F 40/60 131/328 |
| 2017/0150756 A1* | 6/2017 | Rexroad .............. | H05B 1/0244 |
| 2017/0265525 A1 | 9/2017 | Li et al. | |
| 2018/0055091 A1* | 3/2018 | Trzecieski .......... | A61M 15/009 |
| 2018/0084832 A1* | 3/2018 | Li ........................... | A24F 40/40 |

\* cited by examiner

100

100

METHOD AND APPARATUS FOR VAPORIZING LIQUIDS OR THE LIKE WITH A CONCEALABLE VAPORIZER PEN

CROSS REFERENCE TO RELATED APPLICATION(S)

This application is a continuation of U.S. patent application Ser. No. 15/614,127, filed Jun. 5, 2017, which is incorporated by reference as if fully set forth.

FIELD OF INVENTION

The present invention relates generally to electronic vaporizers, and more particularly to compact electronic vaporizers configured to articulate a concealable vaporizer pen for vaporizing liquids or the like.

BACKGROUND

In the area of electronic vaporizers, controlling the voltage of the battery while using and transporting the vaporizer discretely and ergonomically are desirable, yet in current practice, the combination of these amenities is unavailable in one vaporizer. Accordingly, it would be advantageous to implement a vaporizer for the integration of variable voltage control with the ability to enjoy both personal privacy and convenience in operation.

SUMMARY

There is provided according to the embodiments of the invention an apparatus for vaporizing liquids comprising a mechanism for simultaneous deployment of a concealable vaporizer pen and activation of a battery switch. The battery switch is operable to turn on a battery powering a voltage controller configured to select a variable voltage of the battery. The mechanism for simultaneous deployment of the concealable vaporizer pen and activation of the battery may include a button configured for use by the thumb of a user when the apparatus is held in the palm of the user's right hand. The apparatus may further comprise a case configured to contain the battery, wherein the case may have a first compartment configured for concealing the concealable vaporizer pen in a concealed position, a second compartment configured for storing a deployable power adaptor operable to charge the battery, and an attachment means configured for coupling the concealable vaporizer pen to the case. In addition, the deployable power adaptor operable to charge the battery may be a USB adaptor. The case may further comprise an attachment means configured for attachment of the apparatus to a lanyard. The apparatus may have an articulating joint configured to deploy the concealable vaporizer pen in an articulating motion, where the articulating joint may be located on the opposite side of the apparatus from the palm of a user when a right thumb of a user presses on the mechanism.

These and other objects, features and advantages of the present invention will be apparent from the following detailed description of illustrative embodiments thereof, which is to be read in connection with the accompanying drawings.

BRIEF DESCRIPTION OF THE DRAWINGS

The present invention is illustrated by way of example, and not by way of limitation, in the figures of the accompanying drawings in which.

DETAILED DESCRIPTION

Figure 1:
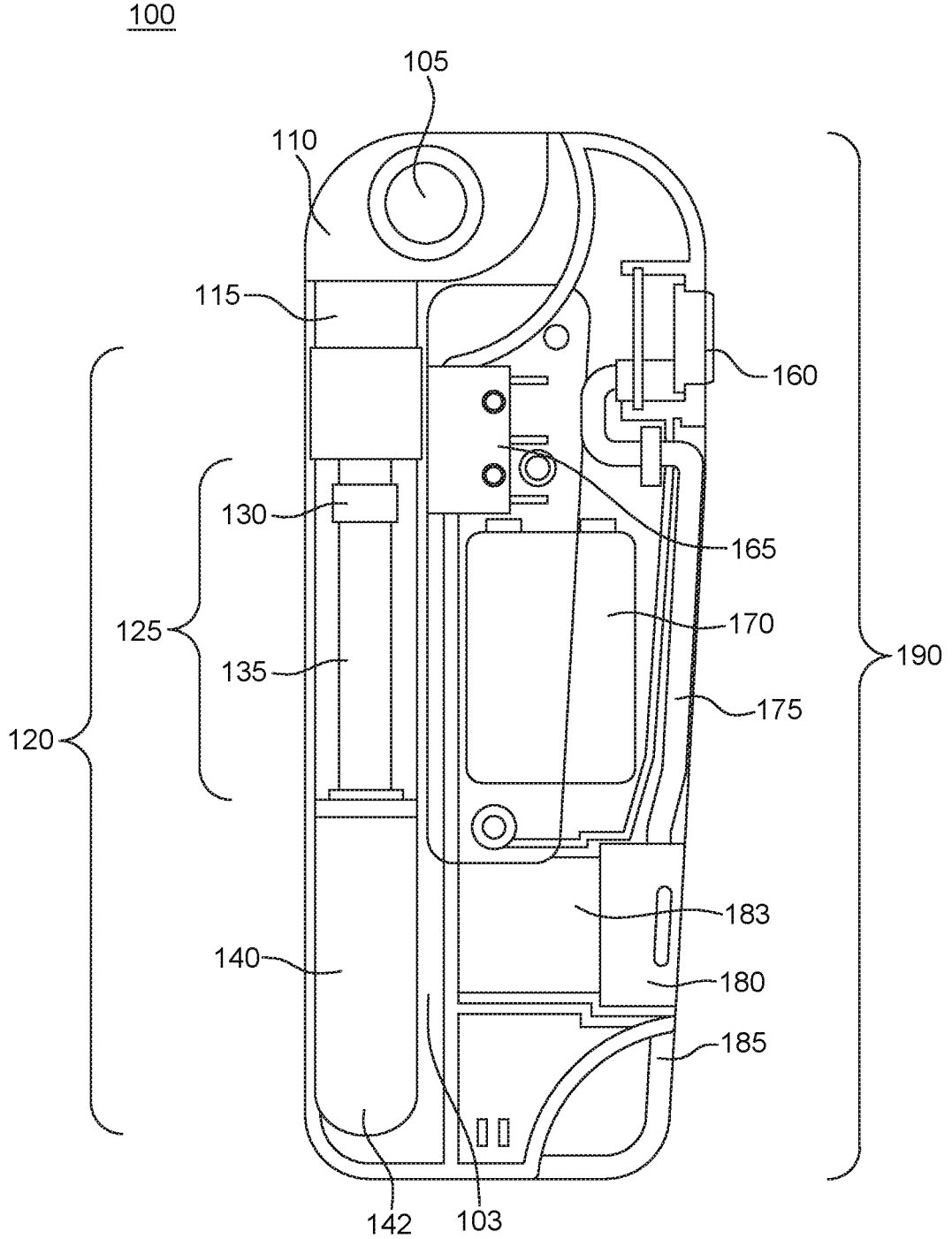
FIG. 1 is a perspective view of an embodiment showing the interior of the front side of a compact electronic vaporizer where the concealable vaporizer pen is in the concealed position.

Various embodiments are described in the following paragraphs. Where like elements have been depicted in multiple embodiments, identical or similar reference numerals have been used for ease of understanding.

In general, a vaporizer device utilizes a battery that powers the heating device or atomizer, which vaporizes a liquid held inside a cartridge. Liquid from the cartridge flows to the atomizer, which is vaporized at a temperature level, determined, in part, by the voltage from the battery. A vaporizer generally utilizes convection heating to heat the air passing through the atomizer to a certain temperature; when the heated air passes through the liquid, the liquid is vaporized.

Particular liquids may be added to the cartridge based upon user preferences, such as flavor and vaporization properties. Because particular flavors of liquid may taste better at different temperatures, variable voltage control of the battery, in combination with additional features, to be detailed in the forthcoming paragraphs, may enhance a user's ability to operate the vaporizer discretely and conveniently. As the ability to control the variable voltage directs the amount of heat generated by the atomizer, a user can determine the vaporization temperature and flavor of particular liquids in the cartridge. Controlling the variable voltage also allows a user to create a certain amount of vapor. In particular, the same amount of vapor may be created at two different temperatures, as the user may take shorter or longer pulls to create the same amount of vapor.

Currently, electronic vaporizers with variable voltage controllers are large and cumbersome in size. A compact electronic vaporizer with variable voltage control configured to articulate a concealable vaporizer pen may enable a user to enjoy vaporization more conveniently. In particular, an articulating pen, concealable inside a protective case within a hand-held variable voltage compact electronic vaporizer, would enhance a user's ability to operate a variable voltage vaporizer in privacy and convenience.

Further, a variable voltage vaporizer may be configured for ergonomic use by a right-handed user. For example, the proposed vaporizer provides for a variable voltage control mechanism that may be activated by the right-hand thumb of the user. An additional feature may include a push button, also configured for ergonomic use by a right-handed user, which simultaneously activates both the concealable articulating vaporizer pen and a battery switch to turn on the vaporizer. The benefit of simultaneous articulation of the pen and power activation eliminates the inconvenience of manipulating an additional, separate power button each time a user activates the vaporizer.

In addition, a mouthpiece with round-tip opening, as opposed to a rectangular opening, may provide greater freedom for orientation of the device during operation. Together, the right-handed configurations and mouthpiece with round-tip opening may enable a user to vaporize more ergonomically.

Referring to FIG. 1, a transparent view of an example compact electronic vaporizer 100 is depicted that provides an improved electronic vaporization device for vaporizing liquids and oils, or the like, and eliminates the need to manually push a separate button to turn on a battery. More specifically, a push button 105 simultaneously releases and thereby articulates the concealable articulating vaporizer pen 120 (also depicted in FIGS. 2 and 3) and activates a battery switch 165 on a battery 170 to turn on the vaporizer 100. In addition, the example compact electronic vaporizer 100 includes a variable voltage controller 160 configured to select a variable voltage of the battery 170. The variable voltage controller 160 provides for an improved vaporization experience as the user can select an optimum temperature or voltage at which to vaporize, depending on the vaporization properties of a given liquid.

Also, the vaporizer 100 includes a dedicated configuration for convenient use by right-handed users with the push button 105 on the same side of the device as the articulating vaporizer pen 120. Referring to FIG. 1 in conjunction with FIG. 5, this configuration allows a user to grip the electronic vaporizer 100 in their right hand, and to deploy the articulating vaporizer pen 120 by pressing the push button 105 with their right thumb, without having their palm block the articulating vaporizer pen 120 from being deployed.

Referring again to FIG. 1, the articulating vaporizer pen 120 of the electronic vaporizer 100 also includes a mouthpiece 140 with round-tip opening 142 that enables a user to position the electronic vaporizer 100 at any angle at their mouth. Together, the right-handed configuration and round-tip opening 142 eliminate cumbersome orientations necessary to hold, manipulate and operate prior art vaporizers. Moreover, the concealable articulating vaporizer pen 120 with protective case 190 conceals the vaporizer pen 120 inside the protective case 190, thereby avoiding buildup of dirt and other debris from the external environment, such as the user's pocket. These and other objects, features and advantages of the example compact electronic vaporizer 100 will be described in further detail in the following illustrative embodiments thereof.

Figure 10:
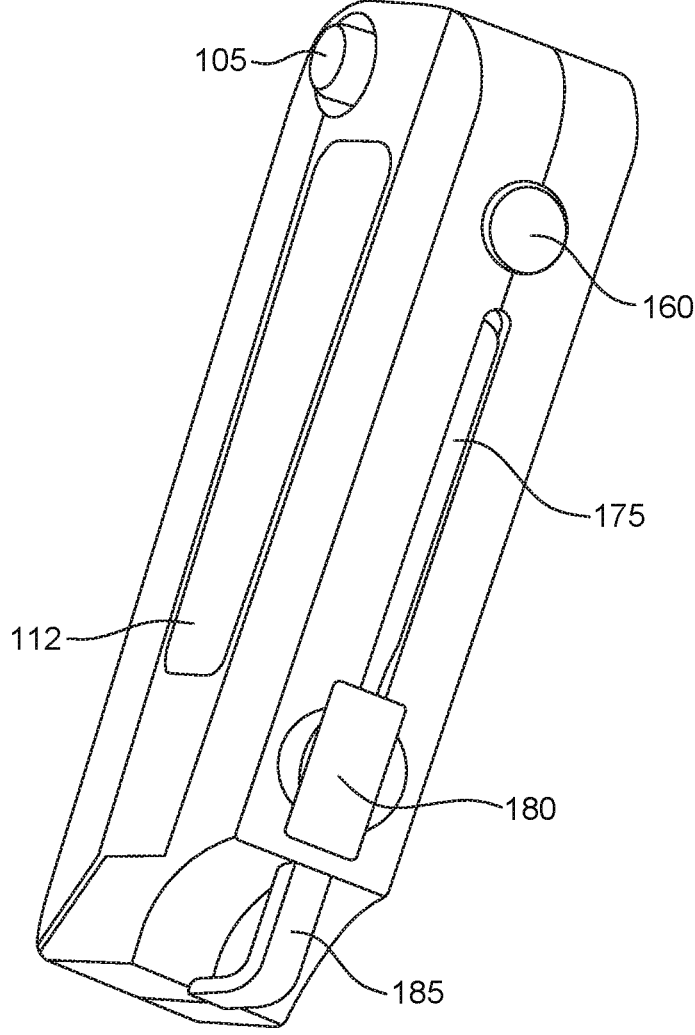
FIG. 10 is a perspective view of an embodiment showing the right side of a compact electronic vaporizer where the deployable power adaptor is in the concealed position.

Referring again to FIG. 1, the protective case 190 of the example compact electronic vaporizer 100 encapsulates the mechanical components of the vaporizer 100. The case is optionally made of a durable, hard substance such as plastic, composite, or metal. The case 190 may include a loop 185 for attachment to a lanyard, mini carabiner or key chain, for example. The case 190 may also be configured to hold a deployable power adaptor, such as a USB power adaptor 180 and an adaptor cord 175. For example, FIG. 10 provides an additional perspective view of an example USB power adaptor 180 and the adaptor cord 175. Referring again to FIG. 1, the USB power adaptor 180 and adaptor cord 175 may be contained within an adaptor compartment 183 inside the case 190. The vaporizer pen 120, as shown in FIG. 1, is depicted in its concealed position inside a pen compartment 103 of the case 190. In particular, the vaporizer pen 120 may include a mouthpiece 140 with a round-tip opening 142 and a cartridge 125 for holding a vaporization liquid chosen by the user. The cartridge 125 may also house a cylindrical tube 135 for inhalation and an atomizer 130 to heat the liquid held inside the cartridge 125. The vaporizer 100 may further include an articulating joint 110 with an attachment means 115 for attaching the vaporizer pen 120 to the joint 110. Further, a push button 105, configured to be pushed by the thumb of a user's right hand, while holding the electronic vaporizer in their palm, may simultaneously deploy the vaporizer pen 120 from its concealed position inside the case 190 and turn on the battery 170 by activating the battery switch 165. Those of skill in the art of electronic vaporization devices would understand that the example compact electronic vaporizer 100 may include additional mechanisms for automatically activating the battery 170, such as sensors that turn on the battery 170 upon detecting inhalation by a user.

Figure 2:
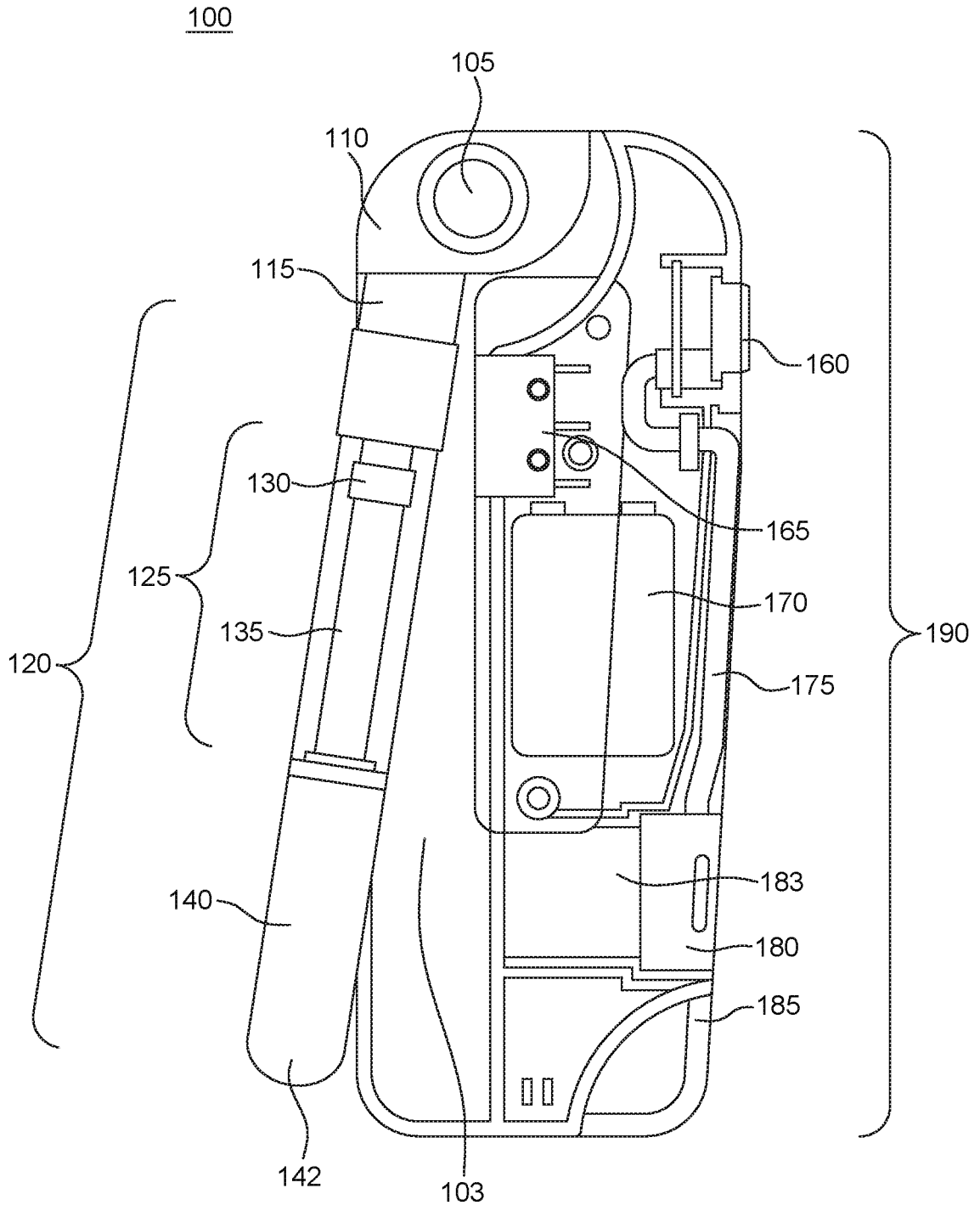
FIG. 2 is a perspective view of an embodiment showing the interior of the front side of a compact electronic vaporizer where the concealable vaporizer pen is in a partially deployed position.
Figure 3:
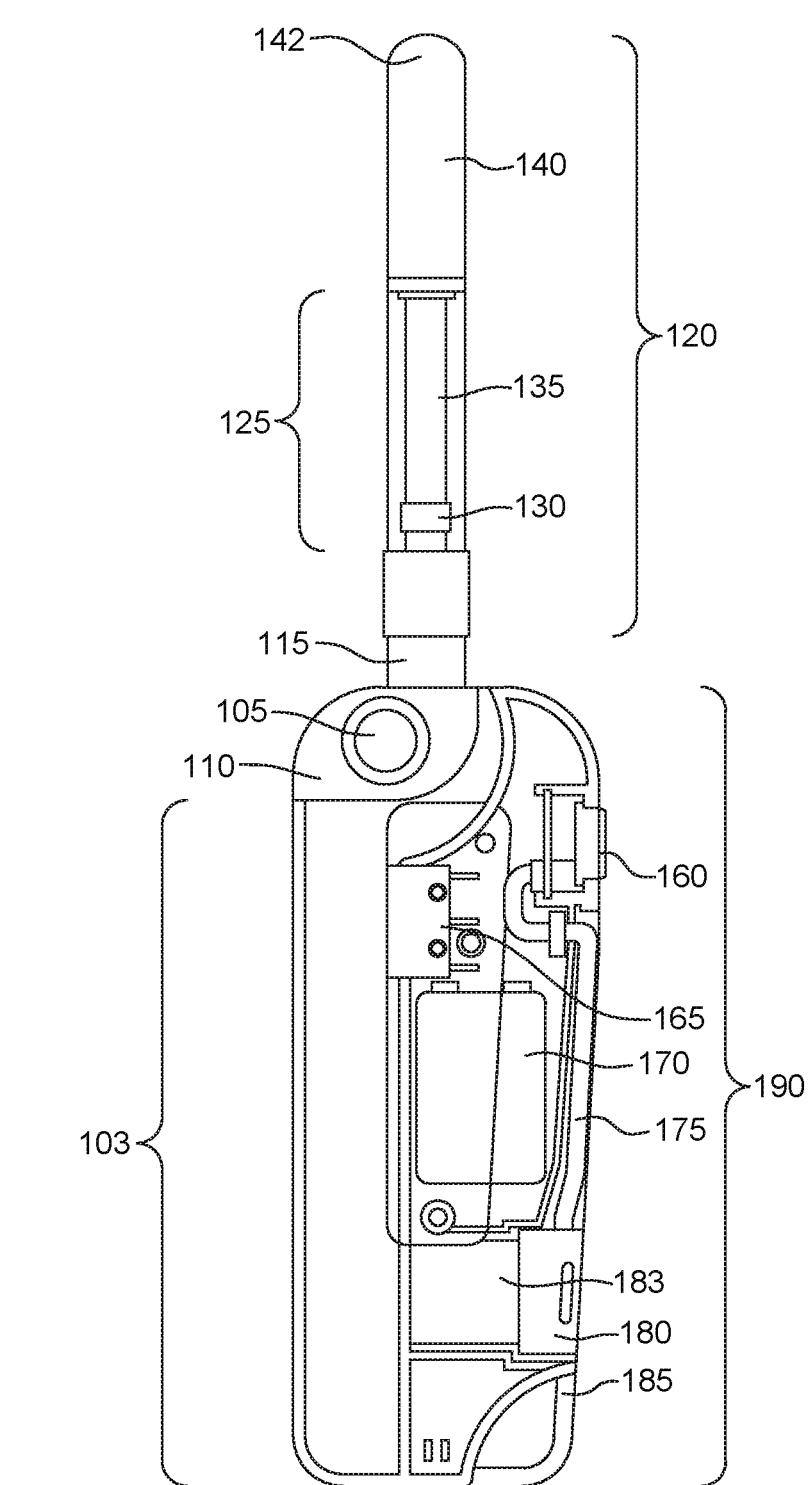
FIG. 3 is a perspective view of an embodiment showing the interior of the front side of a compact electronic vaporizer where the concealable vaporizer pen is in the fully-deployed position.
Figure 4:
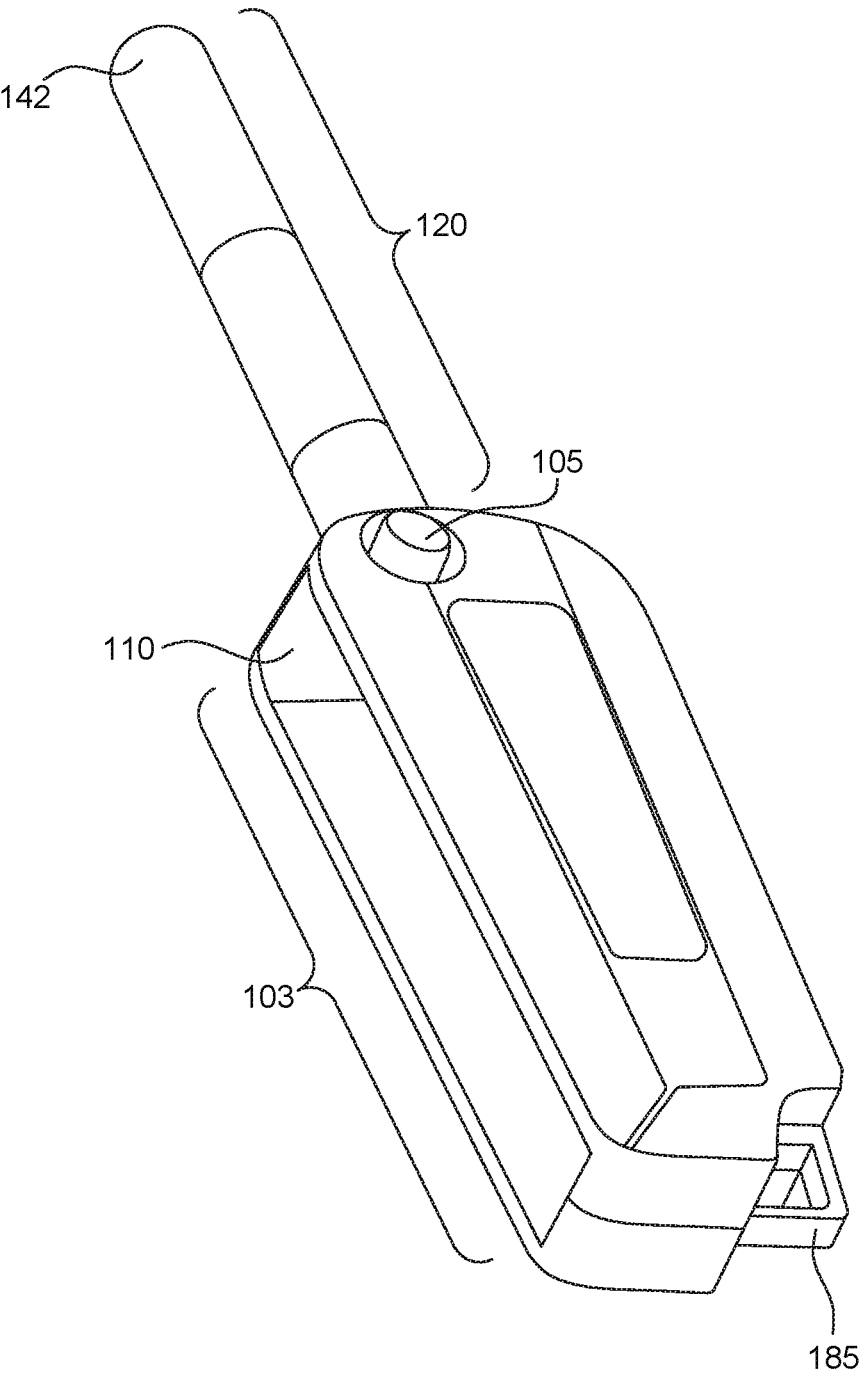
FIG. 4 is a perspective view of an embodiment showing the exterior of the front side of a compact electronic vaporizer where the concealable vaporizer pen is in the fully-deployed position.

Referring to FIG. 2, another transparent view of the example compact electronic vaporizer 100 is depicted showing the vaporizer pen 120 in a partially deployed position outside of the pen compartment 103. Referring to FIG. 3, an additional transparent view of the example compact electronic vaporizer 100 illustrates the vaporizer pen 120 in a fully deployed position outside the pen compartment 103. Further, FIG. 4 shows an external view of the vaporizer pen 120 in its fully deployed position outside the pen compartment 103.

Figure 8:
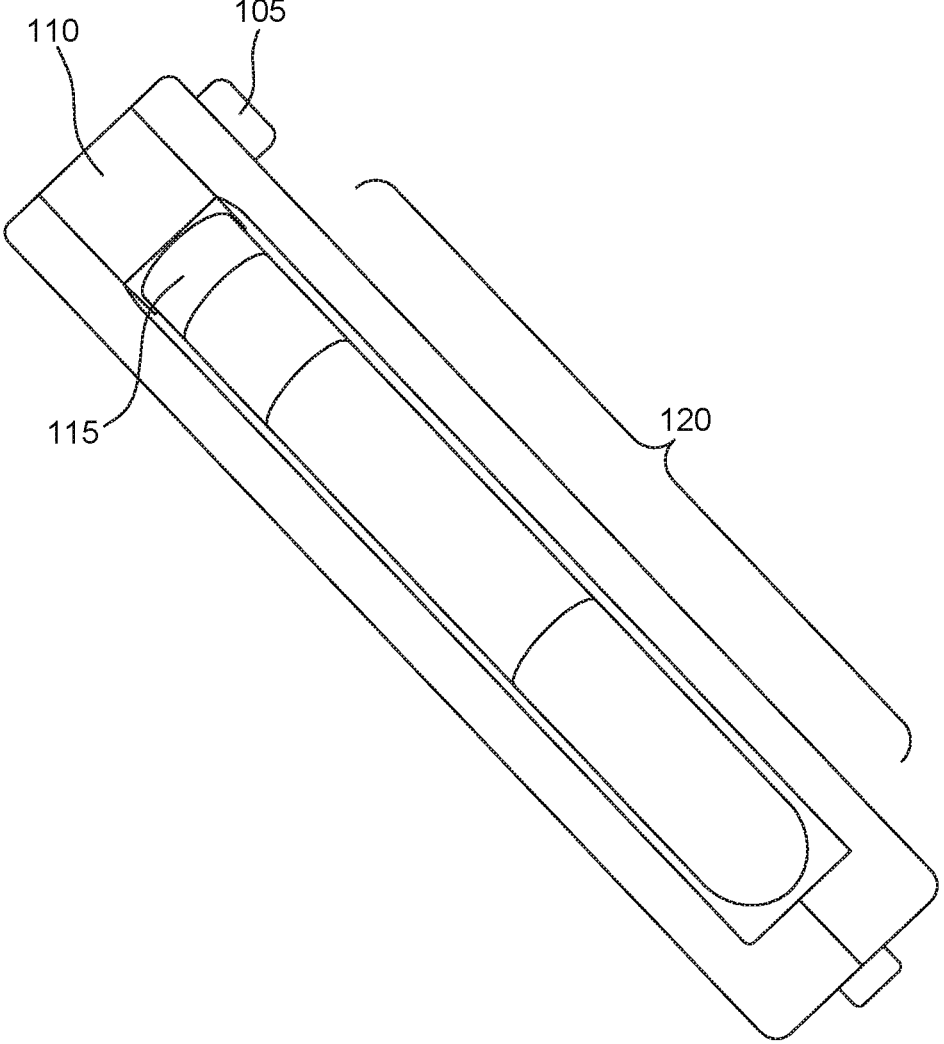
FIG. 8 is a perspective view of an embodiment showing the left side of a compact electronic vaporizer where the concealable vaporizer pen is in the concealed position.
Figure 9:
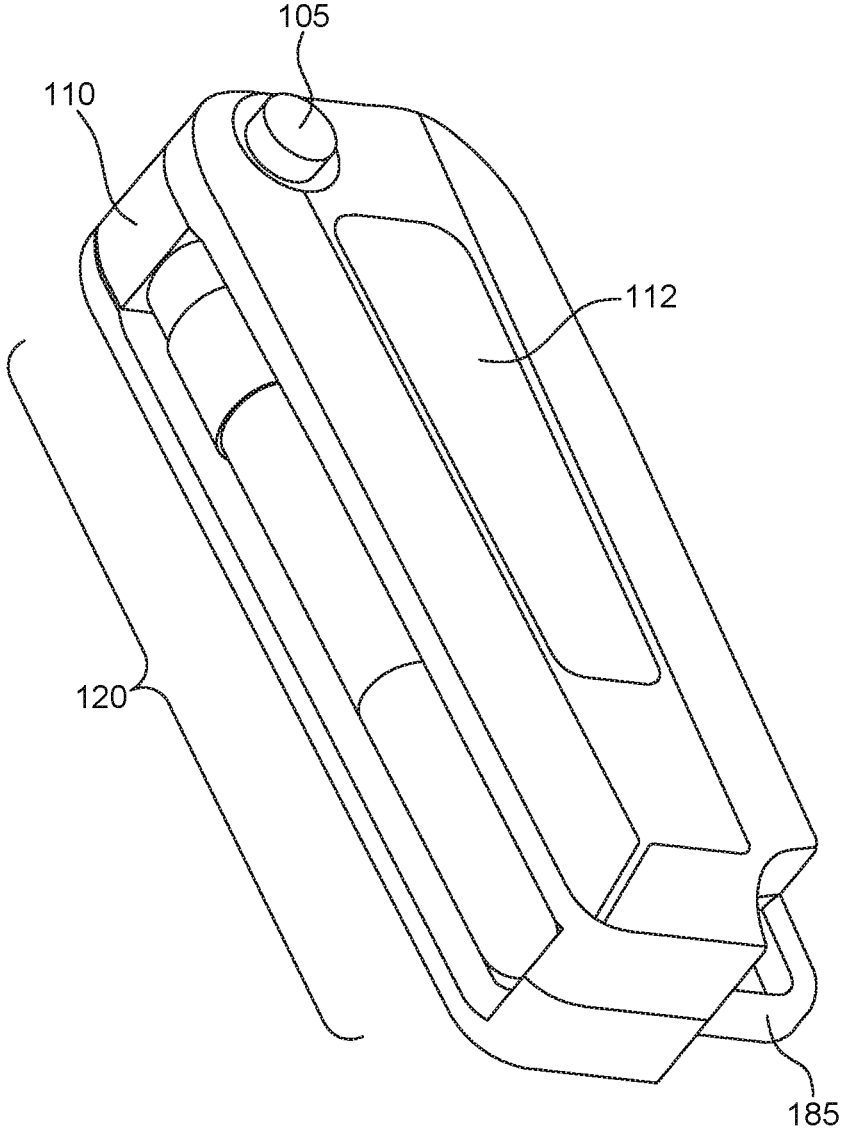
FIG. 9 is an additional perspective view of an embodiment showing the left side of a compact electronic vaporizer where the concealable vaporizer pen is in the concealed position.

Referring again to FIG. 4, the pen compartment 103 inside the case 190 conceals the articulating vaporizer pen 120 when not deployed. This may reduce contact and accumulation of dirt and other undesirable debris, especially pocket lint, when stored in a pocket of a user. Notably, the mouthpieces of prior art vaporizers, and particularly the tips of the mouthpieces, from which users inhale, commonly accumulate dirt and debris, when stored in a user's pocket or otherwise not in use. The electronic vaporizer 100 provides for the concealment of the vaporizer pen 120 inside the pen compartment 103 of the case 190. While concealed inside the pen compartment 103 in the case 190, the mouthpiece 140 with round-tip opening 142 is protected from the accumulation of dirt and debris. As seen in FIGS. 8 and 9, for example, the vaporizer pen 120, when in a concealed position, is protected from dirt and debris.

Figure 5:
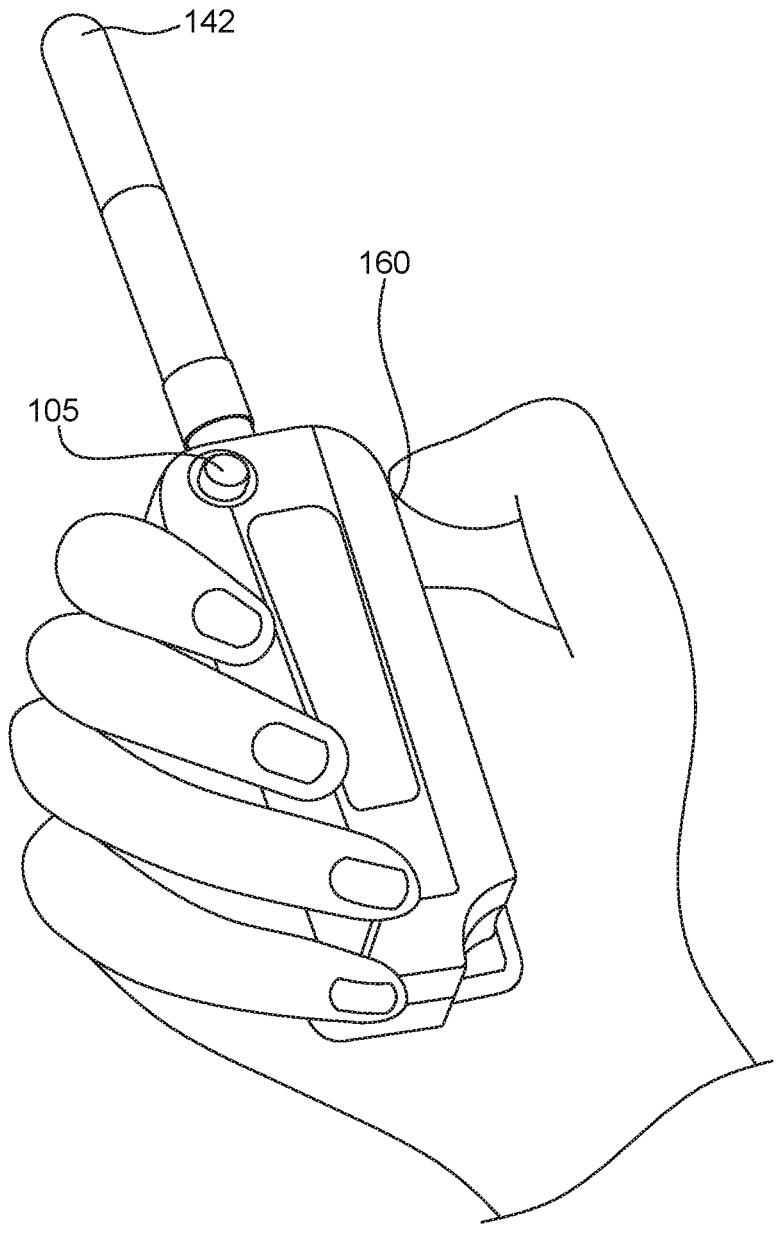
FIG. 5 is a perspective view of an embodiment showing the front side of a compact electronic vaporizer with a button configured for use by a right-handed user where the concealable vaporizer pen is in the fully-deployed position.

In reference to FIG. 5, the mouthpiece 140 with round-tip opening 142 may enable a user to hold the compact electronic vaporizer 100 in any position to inhale from the round-tip opening 142. Current vaporizer devices feature a rectangular tip, which restricts a user's orientation of the vaporizer device in relation to comfortably inhaling from the rectangular or oblong-shaped tip. The electronic vaporizer 100 includes a mouthpiece 140 with round-tip opening 142, thereby allowing a user more freedom for orientation of the compact electronic vaporizer 100 in relation to inhalation from the mouthpiece 140 with round-tip opening 142.

In further reference to FIG. 5, the location of the variable voltage controller 160 and push button 105 are optionally configured on the compact electronic vaporizer 100 to accommodate use by the thumb of a user's right hand. Therefore, in view of FIG. 5, a right-handed user may hold the example compact electronic vaporizer 100 in the user's right palm to accommodate the user's thumb to use both the push button 105 and the variable voltage controller 160. The articulating joint 110 (as shown in FIG. 1) is located on the opposite side of the electronic vaporizer 100 from the user's right palm, thereby allowing the user to depress the push button 105 and deploy the articulating vaporizer pen 120 without adjusting the device or grip in the user's right hand. Of course, it is understood that the location of the variable voltage controller 160 and push button 105 may also be configured on the example compact electronic vaporizer 100 to accommodate use by the thumb of a user's left hand.

Figure 6:
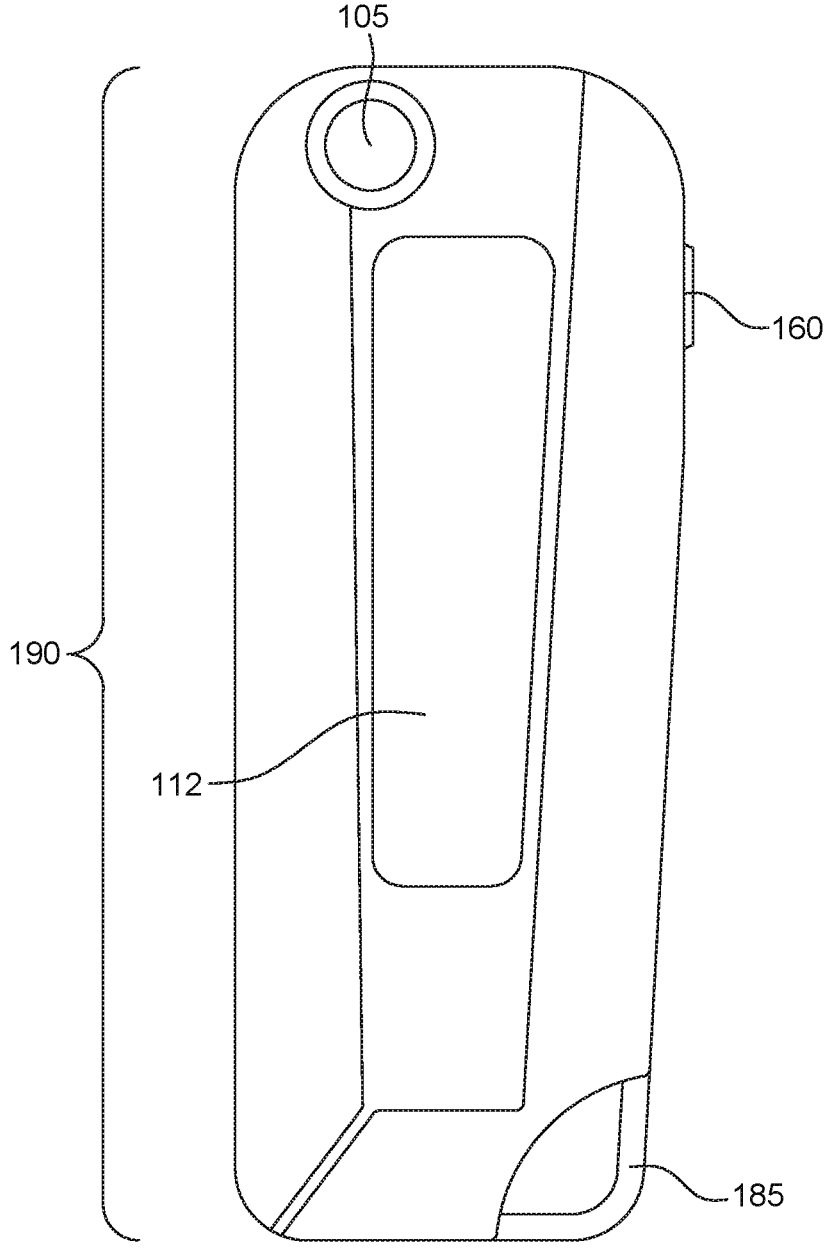
FIG. 6 is a perspective view of an embodiment showing the exterior of the front side of a compact electronic vaporizer where the concealable vaporizer pen is in the concealed position.

Referring to FIG. 6, a frontal perspective view of the example compact electronic vaporizer 100 is shown where the vaporizer pen 120 is in its concealed position inside the protective case 190. The frontal view shows a frontal face 112 of the protective case 190, which may be utilized to display a logo or other ornamental design, for example. Alternatively, the frontal face 112 may be utilized to implement a graphic user interface (GUI) (not shown), to provide the user with information regarding the selected voltage, as controlled by the variable voltage controller 160 configured to select a variable voltage of the battery 170.

Figure 7:
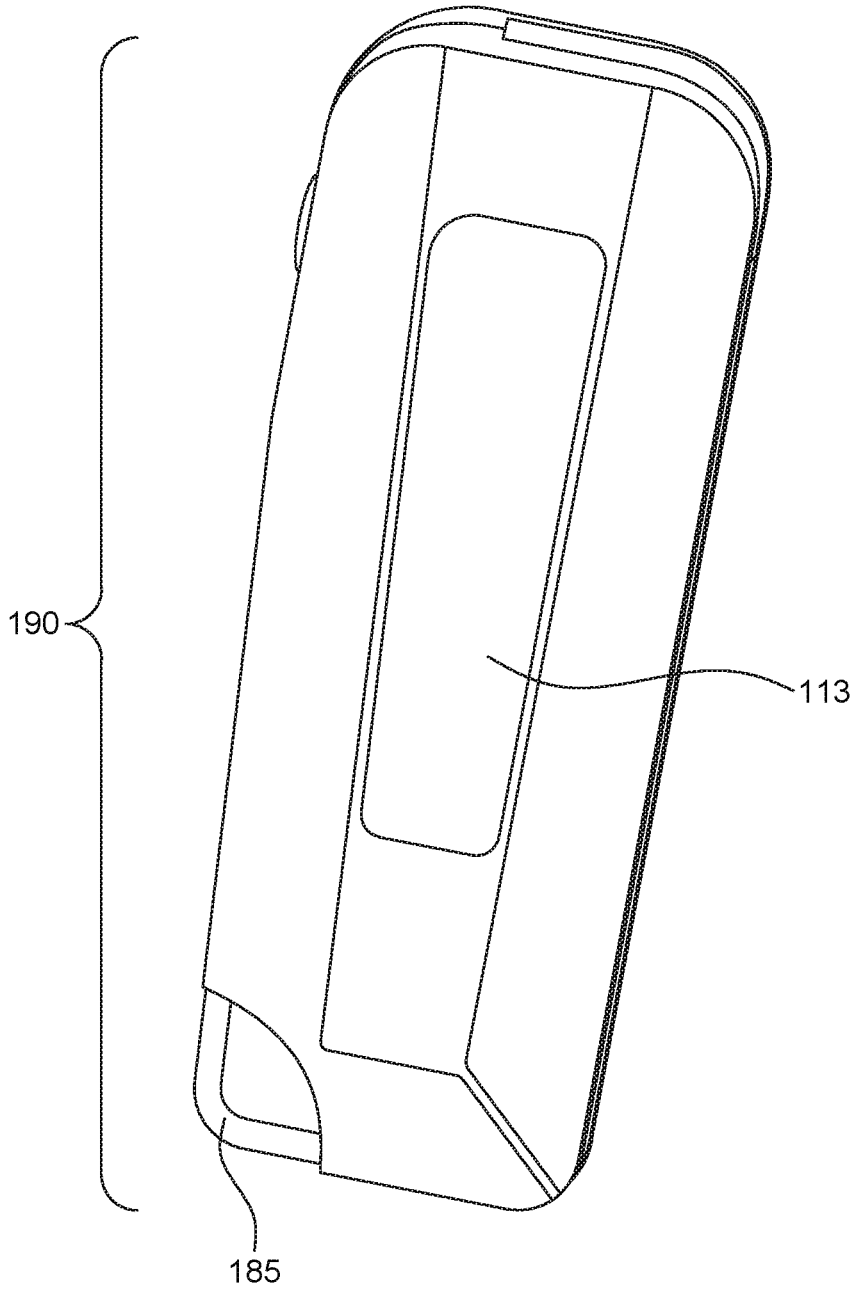
FIG. 7 is a perspective view of an embodiment showing the exterior of the posterior side of a compact electronic vaporizer where the concealable vaporizer pen is in the concealed position.

Referring to FIG. 7, a posterior perspective view of the example compact electronic vaporizer 100 is shown where the vaporizer pen 120 is in its concealed position inside the protective case 190. Similar to the frontal view of FIG. 6, the posterior view of FIG. 7 shows a posterior face 113 of the protective case 190, which may be utilized to display a logo or other ornamental design, for example. Alternatively, the posterior face 113 may be utilized to implement a graphic user interface (GUI) (not shown), to provide the user with information regarding the selected voltage, as controlled by the variable voltage controller 160 configured to select a variable voltage of the battery 170.

Figure 11:
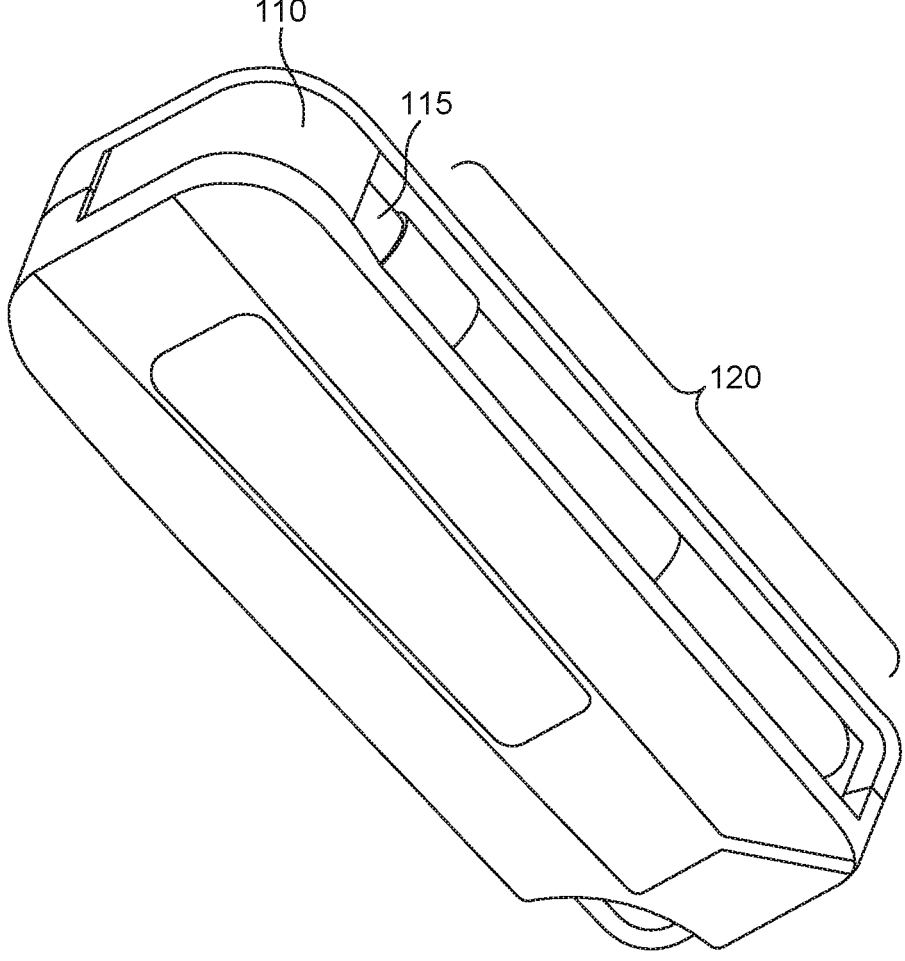
FIG. 11 is a perspective view of an embodiment showing the top side of a compact electronic vaporizer where the concealable vaporizer pen is in the concealed position.

In reference to FIG. 11, an additional perspective view of the example compact electronic vaporizer 100 is shown where the articulating joint 110 with attachment means 115 for attaching the vaporizer pen 120 to the joint 110 is depicted. In conjunction with FIG. 11, the orientation of the joint 110 as it articulates the vaporizer pen 120 is best understood by referring to FIGS. 2 and 3, which illustrate the configuration of the joint 110 inside the protective case 190 during articulation. As it articulates, the joint 110 may activate or contact the battery switch 165 to turn on the battery 170 of the compact electronic vaporizer 100. One of skill in the art will recognize that other configurations and structures that simultaneously deploy the vaporizer pen 120 and turn on the battery 170 are possible.

Figure 12:
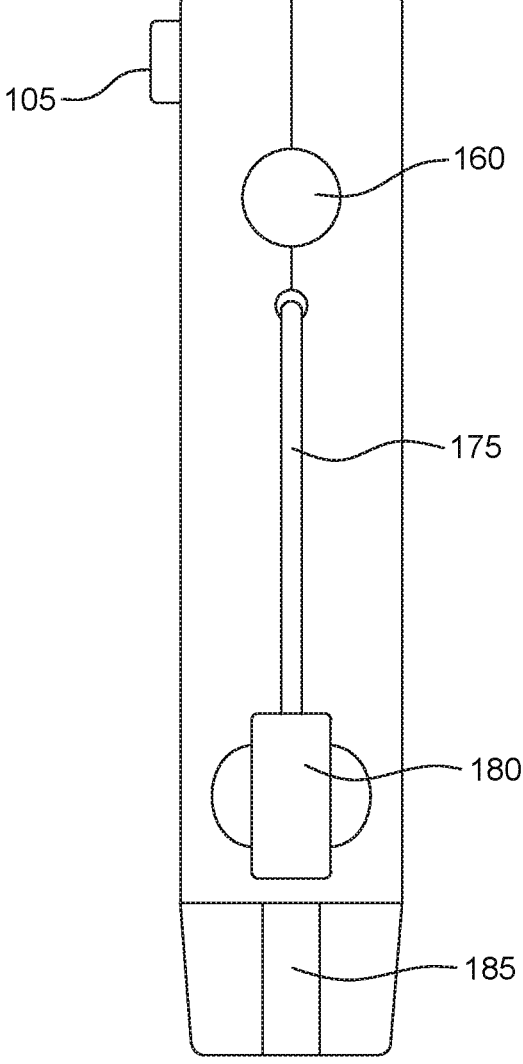
FIG. 12 is an additional perspective view of an embodiment showing the right side of a compact electronic vaporizer where the deployable power adaptor is in the concealed position.

Referring to FIG. 12, a perspective view of the example compact electronic vaporizer 100 is shown to illustrate the variable voltage controller 160. In particular, the variable voltage controller 160 may allow a user to select a particular voltage. For example, depending on the vaporization properties of the liquid chosen by the user for vaporization in the example compact electronic vaporizer 100, a particular voltage might be optimal to vaporize the chosen liquid. Referring to FIG. 12 in conjunction with FIG. 3, the atomizer 130 heats the liquid held inside the cartridge 125 based on the amount of power supplied to the atomizer 130 by the battery 170. Therefore, if the user uses the variable voltage controller 160 to select the highest voltage, then the atomizer 130 will achieve the highest temperature level to vaporize the liquid inside the cartridge 125. The variable voltage controller 160 may be configured to allow the user to select an ideal voltage in the range from 2.9 volts to 4.8 Volts. It is understood that the voltage controller 160 may be configured as a button to select a desired voltage. It is further understood that the voltage controller 160 may optionally be configured as a dial to select a desired voltage.

The variable voltage controller 160 may utilize an indicator light, such as an LED light, to display the chosen power level. Those of skill in the art would understand the implementation of an LED indicator light in combination with the variable voltage controller 160. For example, the variable voltage controller 160 may show a green light for 3.3 Volts, a yellow light for 3.7 Volts, or a red light for 4.3 Volts. It is understood that the indicator light of the variable voltage controller 160 may include additional power levels, aside from 3.3 Volts, 3.7 Volts, or 4.3 Volts. It is further understood that the indicator light of the variable voltage controller 160 may be operable to indicate other parameters of the example compact electronic vaporizer 100. For example, when the battery 170 has been completely charged via the USB power adaptor 180, the indicator light on the variable voltage controller 160 may be green. If the battery 170 is still charging, the indicator light of the variable voltage controller 160 may be red.

Figure 13:
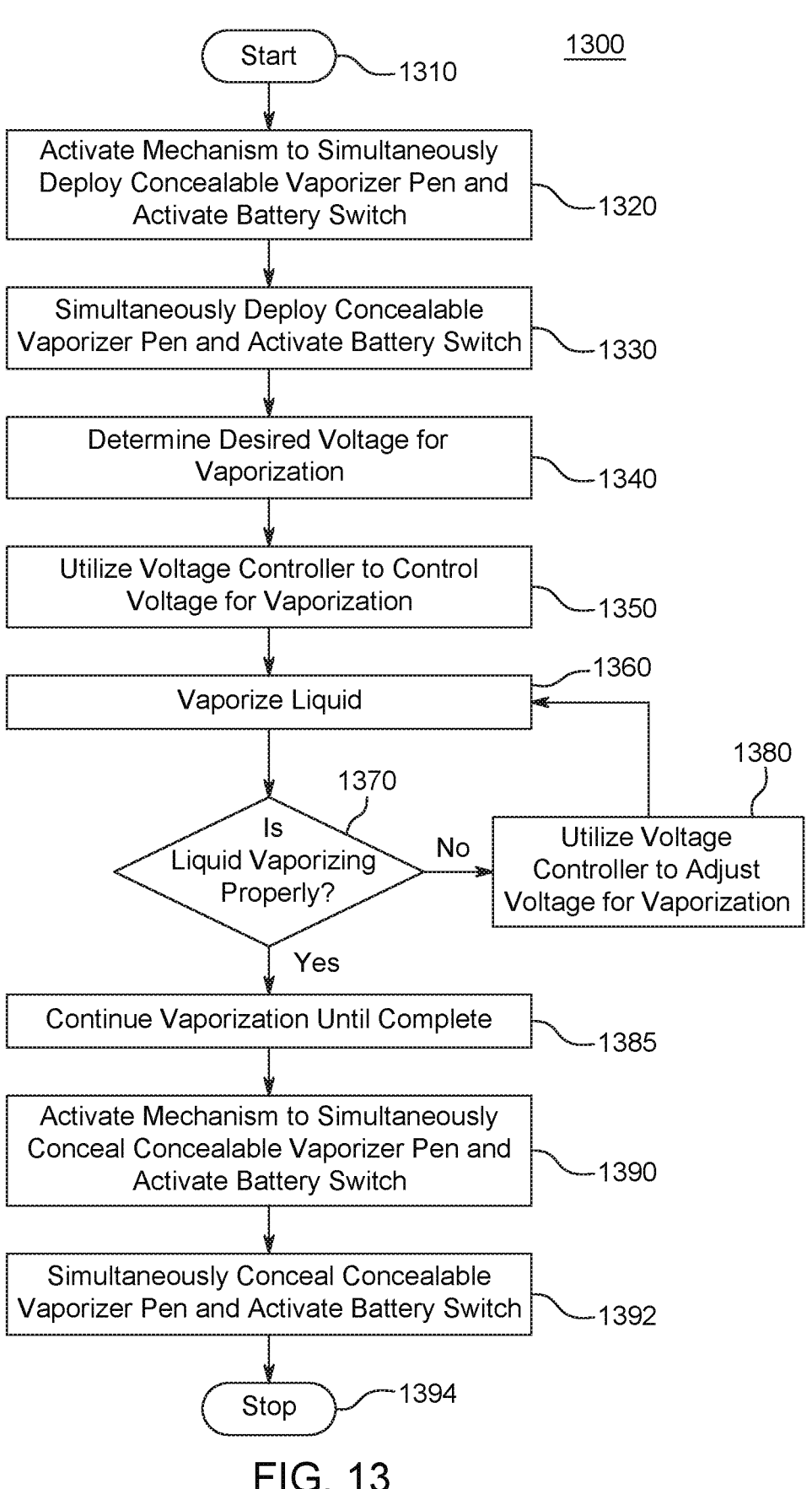
FIG. 13 is a flow diagram of an example vaporization procedure with simultaneous deployment of the concealable vaporizer pen and activation of the battery switch, which is used in conjunction with one or more disclosed embodiments.

Referring to FIG. 13, a flow diagram illustrates an example vaporization procedure 1300 with simultaneous deployment of the concealable vaporizer pen 120 and activation of the battery switch 165. As shown in FIG. 13, the process 1300 begins 1310 by activating the mechanism 1320 for simultaneous deployment of the concealable vaporizer pen 120 and activation of the battery switch 165. As aforementioned, such a mechanism may include the push button 105. Utilizing the mechanism 1320 activates 1330 the simultaneous deployment of the concealable vaporizer pen 120 and activation of the battery switch 165. Thereafter, the user may determine the voltage level 1340 for the atomizer 130 by utilizing the variable voltage controller 160 to select the voltage level 1350. Next, the user may begin vaporizing the liquid 1360 held inside the cartridge 125 based on the chosen voltage level supplied to the atomizer 130 by the battery 170. After a user has commenced vaporization of the liquid 1360, a determination will be made whether the vaporization is proceeding properly (step 1370). If it is determined that the liquid requires a different voltage to vaporize properly, then the user may utilize the variable voltage controller 160 to adjust the voltage, thereby adjusting the voltage or temperature of vaporization 1380, and return to vaporization at step 1360. If it is determined that the voltage or temperature of vaporization at step 1370 is acceptable, then the user may continue to vaporize the liquid in the cartridge 125, until vaporization is complete 1385. Upon completion of vaporization at step 1385, a user can finish the procedure 1300 by activating the mechanism 1390 for simultaneous concealment of the concealable vaporizer pen 120 and activation of the battery switch 165 (step 1390) to turn off the batter 170. Upon the simultaneous concealment of the concealable vaporizer pen 120 and activation of the battery switch 165 (step 1392), the procedure 1300 is complete 1394.

Although features and elements are described above in particular combinations, each feature or element can be used alone without the other features and elements or in various combinations with or without other features and elements.

What is claimed is:

1. An apparatus for vaporizing liquids, the apparatus comprising:

a case;

a concealable vaporizer pen that includes a mouthpiece, an atomizer, and a removable cartridge, the concealable vaporizer pen configured to be deployed from a concealed position inside the case to a deployed position outside the case, the mouthpiece, the atomizer and the removable cartridge each disposed outside of the case when the concealable vaporizer pen is in the deployed position;

an articulating joint configured to connect the concealable vaporizer pen including the mouthpiece, atomizer, and the removable cartridge to the case, wherein the entire concealable vaporizer pen is deployed in an articulating motion from the concealed position inside the case to the deployed position outside the case;

a battery configured for activation upon deployment of the concealable vaporizer pen to the deployed position outside the case and deactivation upon deployment of the concealable vaporizer pen to the concealed position inside the case;

a single push-button voltage controller configured to select one of at least three predetermined voltages provided by the battery to the atomizer and maintain the selected voltage during vaporization; and an indicator display that is a light emitting diode (LED) display, wherein the removable cartridge is not removable in the concealed position, wherein the removable cartridge is removable in the deployed position, and wherein the indicator display is configured to display one of three colors configured to indicate the one of at least three predetermined voltages.

2. The apparatus of claim 1, wherein the at least three predetermined voltages provided by the battery are in a range from 2.9 volts to 4.8 Volts.

3. The apparatus of claim 1, wherein the at least three predetermined voltages provided by the battery are 3.3 Volts, 3.7 Volts, and 4.3 Volts.

4. The apparatus of claim 1 further comprising an indicator display configured to display the selected voltage provided to the atomizer.

5. The apparatus of claim 1, wherein the indicator is configured to display a green light to indicate a selection of 3.3 Volts, a yellow light to indicate a selection of 3.7 Volts, or a red light to indicate a selection of 4.3 Volts.

6. The apparatus of claim 1, further comprising a deployment mechanism on the case configured to deploy a concealable vaporizer pen, wherein the deployment mechanism is configured for use by the thumb of a user when the apparatus is held in the palm of the user's right hand.

7. The apparatus of claim 6, wherein the concealable vaporizer pen is deployed in response to pushing the deployment mechanism.

8. The apparatus of claim 7, wherein the articulating joint is located on the opposite side of the apparatus from the palm of a user when a right thumb of a user pushes the deployment mechanism.

9. The apparatus of claim 1, wherein the case further comprises:

a first compartment configured to conceal the concealable vaporizer pen in the concealed position; and a second compartment configured to store a deployable power adaptor operable to charge the battery.

10. The apparatus of claim 9, wherein the deployable power adaptor operable to charge the battery is a USB power adaptor.

11. The apparatus of claim 1, wherein the case further comprises an attachment means configured to attach the apparatus to a lanyard.

12. The apparatus of claim 1, wherein the mouthpiece further comprises an inhalation end, wherein the inhalation end of the mouthpiece is round.

13. The apparatus of claim 1, wherein the predetermined voltage provided by the battery to the atomizer is associated with a temperature of an atomizer.

14. An apparatus for vaporizing liquids, the apparatus comprising:

a case;

a concealable vaporizer pen that includes a mouthpiece, an atomizer, and a removable cartridge, the entire concealable vaporizer pen configured to be deployed from a concealed position inside the case to a deployed position outside the case, a battery configured for activation upon deployment of the concealable vaporizer pen to the deployed position outside the case and deactivation upon deployment of the concealable vaporizer pen to the concealed position inside the case;

a single push-button voltage controller configured to select one of at least three predetermined voltages provided by the battery to the atomizer and maintain the selected voltage during vaporization, and an indicator display that is a light emitting diode (LED) display, wherein the removable cartridge is not removable in the concealed position, wherein the removable cartridge is removable in the deployed position, and wherein the indicator display is configured to display one of three colors configured to indicate the one of at least three predetermined voltages.

15. The apparatus of claim 14, further comprising a deployment mechanism on the case configured to deploy the concealable vaporizer pen, wherein the deployment mechanism is configured for use by the thumb of a user when the apparatus is held in the palm of the user's right hand.

16. The apparatus of claim 15 wherein the concealable vaporizer pen is deployed in response to pushing the deployment mechanism.

17. The apparatus of claim 14, further comprising an articulating joint configured to connect the concealable vaporizer pen including the mouthpiece and the removable cartridge to the case, wherein the concealable vaporizer pen is deployed in an articulating motion from the concealed position inside the case to the deployed position outside the case.

18. The apparatus of claim 17, further comprising a deployment mechanism on the case configured to deploy the concealable vaporizer pen, wherein the concealable vaporizer pen is deployed in response to pushing the deployment mechanism.

19. The apparatus of claim 17, wherein the articulating joint is located on the opposite side of the apparatus from the palm of a user when a right thumb of a user pushes the deployment mechanism.

20. The apparatus of claim 14, wherein the case further comprises:

a first compartment configured to conceal the concealable vaporizer pen in the concealed position; and a second compartment configured to store a deployable power adaptor operable to charge the battery.

\* \* \* \* \*